United States Patent
Lee et al.

(10) Patent No.: US 12,020,812 B2
(45) Date of Patent: Jun. 25, 2024

(54) SYSTEM AND METHOD FOR PREDICTION OF INTRADIALYTIC ADVERSE EVENT AND COMPUTER READABLE MEDIUM THEREOF

(71) Applicant: National Yang Ming Chiao Tung University, Taipei (TW)

(72) Inventors: Oscar Kuang-Sheng Lee, Taipei (TW); Chih-Yu Yang, Taipei (TW); Yi-Shiuan Liu, Taipei (MY)

(73) Assignee: National Yang Ming Chiao Tung University, Taipei (TW)

( * ) Notice: Subject to any disclaimer, the term of this patent is extended or adjusted under 35 U.S.C. 154(b) by 311 days.

(21) Appl. No.: 17/488,465

(22) Filed: Sep. 29, 2021

(65) Prior Publication Data
US 2023/0094657 A1    Mar. 30, 2023

(51) Int. Cl.
*G16H 40/63*    (2018.01)
(52) U.S. Cl.
CPC .................. *G16H 40/63* (2018.01)
(58) Field of Classification Search
CPC ....................................... G16H 40/63
See application file for complete search history.

(56) References Cited

U.S. PATENT DOCUMENTS

| | | | | |
|---|---|---|---|---|
| 10,342,910 B2* | 7/2019 | Atallah | ............... | A61M 1/1613 |
| 11,615,341 B2* | 3/2023 | Aminzadeh | ............ | G06N 20/00 |
| | | | | 706/12 |
| 2020/0118036 A1* | 4/2020 | Karnagel | ............... | G06N 3/088 |
| 2021/0150412 A1* | 5/2021 | Rashidi | .................. | G06N 20/00 |
| 2021/0193317 A1* | 6/2021 | Kotanko | ................. | A61M 1/14 |
| 2021/0398129 A1* | 12/2021 | Sharma | .................. | G06N 3/045 |
| 2022/0121994 A1* | 4/2022 | Sun | ......................... | G06N 20/00 |
| 2022/0414504 A1* | 12/2022 | Xu | .......................... | G06N 20/00 |
| 2023/0018668 A1* | 1/2023 | Varasani | ............ | A61M 1/1605 |

OTHER PUBLICATIONS

Magee, Colm C., J. Kevin Tucker, and Ajay K. Singh, eds. Core concepts in dialysis and continuous therapies. Springer, 2016. (Year: 2016).*
Liu, et al. "Machine Learning Analysis of Time-Dependent Features for Predicting Adverse Events During Hemodialysis Therapy: Model Development and Validation Study", J Med Internet Res 2021, Published Sep. 7, 2021.

* cited by examiner

*Primary Examiner* — Jason S Tiedeman
*Assistant Examiner* — Ashley Elizabeth Evans
(74) *Attorney, Agent, or Firm* — Amin, Turocy & Watson, LLP

(57) ABSTRACT

Provided are a system and a method for prediction of an intradialytic adverse event, where a machine learning model of two-class classification is utilized to predict intradialytic adverse events in quasi-real time, such that features extracted in an ongoing hemodialysis process in real time can have the hemodialysis session alerted for forthcoming adverse events. Therefore, clinicians can be warned to take necessary actions and adjust the hemodialysis machine settings in advance. In addition, a computer readable medium thereof is also provided.

19 Claims, 8 Drawing Sheets

SYSTEM AND METHOD FOR PREDICTION OF INTRADIALYTIC ADVERSE EVENT AND COMPUTER READABLE MEDIUM THEREOF

TECHNICAL FIELD

The present disclosure relates to medical monitoring application, and more particularly to systems and methods for prediction of intradialytic adverse events in real-time and computer readable media thereof.

DESCRIPTION OF RELATED ART

Hemodialysis (HD) therapy has a substantial role in care management. Due to oliguria or even anuria, most patients with renal failure require fluid removal during HD therapy (HD session) to maintain a euvolemic status. The volume-dependent component of hypertension may be corrected by fluid removal, but the ultrafiltration process exposes HD patients to the risks of hemodynamic instability, which may lead to fatal consequences such as cardiac arrest. Intradialytic hypotension is the most frequent complication during HD and has been identified as a cause of reduced HD efficacy. Acutely, intradialytic adverse events can be fatal; chronically, frequent intradialytic adverse events increase patient morbidity and long-term all-cause mortality.

Monitor Device (e.g., CRIT-LINE® Monitor by FRESENIUS MEDICAL CARE) has been developed to assist with fluid removal during ultrafiltration by noninvasively monitoring real-time hematocrit, oxygen saturation, and intradialytic volume status, using an optical transmission method. Although uncontrolled studies have suggested that this device reduced intradialytic symptoms and assisted in the assessment of target weight, an unblinded randomized controlled trial showed a higher hospitalization rate in the Crit-Line group than in the control group.

Artificial intelligence has also been applied to HD patients to assist clinical practices such as prediction of urea clearance, dietary protein intake, volume status, erythropoiesis-stimulating agent response, iron supplement response, hemoglobin level, HD quality, mortality, etc. Even though artificial intelligence has also been applied to predict intradialytic hypotension risks, previous studies for this application still lack consideration of time-series data input.

Therefore, there is still an unmet need for this technical field to consider time-series data in a machine learning approach to predict intradialytic adverse events more than hypotension risks in an unbiased manner.

SUMMARY

In view of the foregoing, the present disclosure provides a system for prediction of an intradialytic adverse event, comprising: a feature extraction module configured to collect and process data regarding a hemodialysis session of a patient; and a model building and optimization module configured to build a machine learning model based on the data to predict intradialytic adverse events during the hemodialysis session.

The present disclosure also provides a method for predicting an intradialytic adverse event, comprising: configuring a feature extraction module to collect and process data regarding a hemodialysis session of a patient; and configuring a model building and optimization module to build a machine learning model based on the data to predict intradialytic adverse events during the hemodialysis session.

In at least one embodiment of the present disclosure, the data regarding the hemodialysis session of the patient comprise one or more of demographic information, physiological data, dialysis data and registered intradialytic adverse events.

In at least one embodiment of the present disclosure, the data comprise a data set having a plurality of records with measurements at a corresponding timestamp.

In at least one embodiment of the present disclosure, the feature extraction module collects and processes the data regarding the hemodialysis session of the patient by deriving at least one of mean, standard deviation of the mean, coefficient of variance, and slope and R square of linear regression from the measurements as features of the plurality of records.

In at least one embodiment of the present disclosure, the measurements include venous pressure and transmembranous pressure, and the feature extraction module collects and processes the data regarding the hemodialysis session of the patient by deriving at least one of maximum, minimum, and mean of change rate, and second-order derivative of the measurements of the venous pressure and the transmembranous pressure as features of the plurality of records.

In at least one embodiment of the present disclosure, the machine learning model is built on a basis of a first dimension regarding targeted intradialytic adverse events for prediction and a second dimension regarding targeted time periods during the hemodialysis session for prediction.

In at least one embodiment of the present disclosure, the machine learning model is trained by the data labeled with outcome related to the intradialytic adverse events.

In at least one embodiment of the present disclosure, the machine learning model is trained by a key feature combination extracted from the data.

In at least one embodiment, the system of the present disclosure further comprises a data storage module configured to store the data, and the method of the present disclosure further comprises configuring a data storage module to store the data.

The present disclosure further provides a computer readable medium, which stores a computer executable code, and the computer executable code implements the method mentioned above after being executed.

BRIEF DESCRIPTION OF THE DRAWINGS

The present disclosure can be more fully understood by reading the following descriptions of the embodiments, with reference made to the accompanying drawings, wherein.

DETAILED DESCRIPTION OF THE EMBODIMENTS

Figure 1:
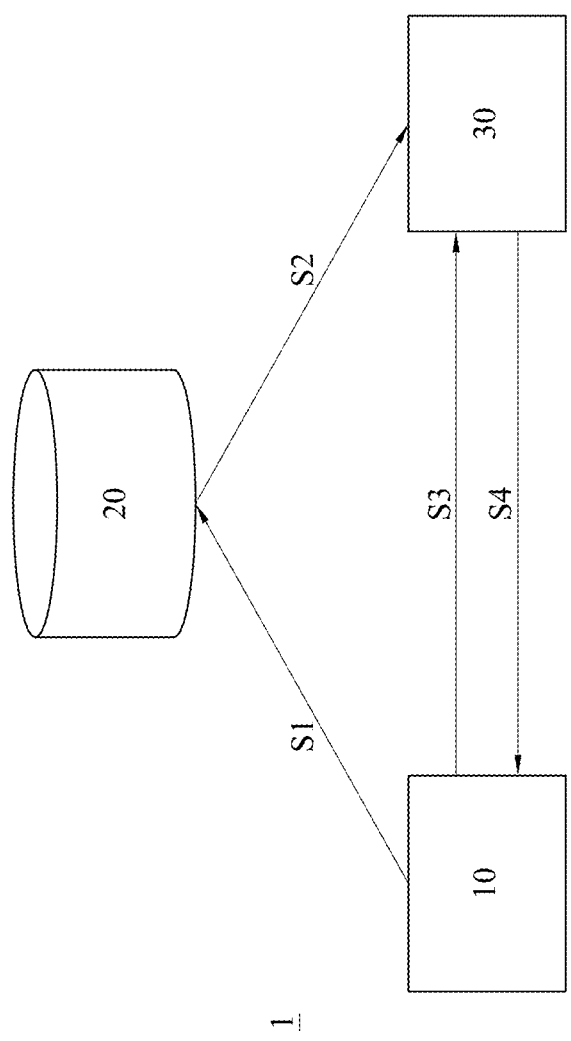
FIG. 1 is a schematic diagram illustrating an exemplifying structure of the system for prediction of an intradialytic adverse event in accordance with embodiments of the present disclosure.

The following embodiments are provided to illustrate the present disclosure in detail. A person having ordinary skill in the art can easily understand the advantages and effects of the present disclosure after reading this disclosure, and also can implement or apply in other different embodiments. Therefore, any element or method within the scope of the present disclosure disclosed herein can combine with any other element or method disclosed in any embodiment of the present disclosure.

The proportional relationships, structures, sizes and other features shown in accompanying drawings of this disclosure are only used to illustrate embodiments described herein, such that those with ordinary skill in the art can read and understand the present disclosure therefrom, of which are not intended to limit the scope of this disclosure. Any changes, modifications, or adjustments of said features, without affecting the designed purposes and effects of the present disclosure, should all fall within the scope of technical content of this disclosure.

As used herein, when describing an object "comprises," "includes" or "has" a limitation, unless otherwise specified, it may additionally encompass other elements, components, structures, regions, parts, devices, systems, steps, connections, etc., and should not exclude others.

As used herein, sequential terms, such as "first," "second," etc., are only cited in convenience of describing or distinguishing limitations such as elements, components, structures, regions, parts, devices, systems, etc. from one another, which are not intended to limit the scope of this disclosure, nor to limit spatial sequences between such limitations. Further, unless otherwise specified, wordings in singular forms such as "a," "an" and "the" also pertain to plural forms, and wordings such as "or" and "and/or" may be used interchangeably.

As used herein, the terms "subject," "individual" and "patient" may be interchangeable and refer to an animal, e.g., a mammal including the human species. The term "subject" is intended to refer to both the male and female gender unless one gender is specifically indicated.

As used herein, the terms "comprise," "comprising," "include," "including," "have," "having," "contain," "containing," or any other variations thereof are intended to cover a non-exclusive inclusion. For example, a composition, mixture, process or method that comprises a list of elements is not necessarily limited to only those elements, but may include other elements not expressly listed, or inherent to such composition, mixture, process, or method.

As used herein, the phrase "at least one," in reference to a list of one or more elements, should be understood to mean at least one element selected from any one or more of the elements in the list of elements, but not necessarily including at least one of each and every element listed within the list of elements and not excluding any combinations of elements in the list of elements. This definition also allows that elements may optionally be present other than the elements identified within the list of elements to which the phrase "at least one" refers, whether related or unrelated to those elements identified. Thus, as a non-limiting example, "at least one of A and B" (or, equivalently, "at least one of A or B," or, equivalently, "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements).

As used herein, the terms "one or more" and "at least one" may have the same meaning and include one, two, three, or more.

As used herein, the terms "measuring" and "measurement" may be interchangeable with "determining," "assessing," "assaying," "detecting" and the like that refer to both quantitative and qualitative determinations. Where a quantitative determination is intended, the phrase "measuring an amount" and the like may be used. Where either a qualitative or quantitative determination is intended, the phrase "measuring a level" or "determining a level" may be used.

Referring to FIG. 1, a system 1 for prediction of an intradialytic adverse event is illustrated, comprising: a feature extraction module 10, a data storage module 20, and a model building and optimization module 30. Described elements of the system 1 may be connected to each other via any suitable wired or wireless means, of which the present disclosure is not limited thereto.

In some embodiments, the feature extraction module 10 may be coupled to or implemented in a hemodialysis (HD) machine (not shown), such that any records derived from a patient during HD sessions may be collected for feature extraction on-site.

In some embodiments, the data storage module 20 is configured to maintain data received and processed by the feature extraction module 10, so as to provide for data inspection and/or model building in a later stage. The data storage module 20 may be realized as any suitable data storing device, system, database, cloud storage, or the like, of which the present disclosure is not limited thereto.

In some embodiments, the model building and optimization module 30 is configured to build a machine learning model for predicting intradialytic adverse events of patients, and/or improve performance of said machine learning model based on improved data quality from HD sessions of the patients. In at least one embodiment, more than one machine learning model may be built by the model building and optimization module 30, so as to cope with various characteristics of the data collected by the feature extraction module 10. For example, machine learning model(s) may be built on the basis of two dimensions: targeted intradialytic adverse events for prediction (e.g., blood pressure elevation, muscle cramp and all events except blood pressure elevation); and targeted time periods during HD sessions for prediction (e.g., different 30-minute periods during HD sessions). However, the number and prediction target of machine learning models being built is not meant to limit the scope of the present disclosure, and can be altered in any suitable approaches based on design requirements.

In some embodiments, the elements of the system may be individually realized as any suitable computing device, apparatus, program, system, or the like, but the present disclosure is not limited thereto. For example, any two or three of the feature extraction module 10, the data storage module 20 and the model building and optimization module 30 may be integrated instead of being realized as three distinct units. In some embodiments, said three elements may also be integrated and realized in a cloud computing environment. Nevertheless, without straying from the operation philosophy of the present disclosure, the configuration of said elements of the system may be realized in any suitable forms and should not be restrictive to the scope of the present disclosure.

Further described in FIG. 1 is operation relationships between said elements of the system 1, which are denoted as arrows (described as "step(s)" herein) and explained herefrom.

In some embodiments, step S1 denotes that the feature extraction module 10 will collect and process data regarding records of patients during HD sessions in real time and store said data in the data storage module 20.

In some embodiments, step S2 denotes that the model building and optimization module 30 will utilize the data stored in the data storage module 20 to build and/or optimize a machine learning model for predicting intradialytic adverse events of patients. For example, the machine learning model may be based on any one of linear model, random forest support vector regression, XGBoost, LASSO regression, ensemble method, deep learning or the like or any arbitrary combination of those mentioned above, of which the present disclosure is not limited thereto.

In some embodiments, step S3 denotes that for a fully trained machine learning model built by the model building and optimization module 30, the feature extraction module 10 will also send data regarding records of patients during HD sessions to said machine learning model for predicting intradialytic adverse events in real time.

In some embodiments, step S4 denotes that after the machine learning model has completed its prediction, the prediction result will be sent back to the feature extraction module 10 (or the HD machine it coupled thereto) to inform of the risk of an intradialytic adverse event of the patient.

In some embodiments, a computer readable medium is also present, which stores a computer executable code, and the computer executable code is configured to realize the steps as discussed in this disclosure after being executed.

From here, a detailed description of how working mechanisms of the feature extraction module 10, the data storage module 20, and the model building and optimization module 30 are designed will be provided.

Methodology

Study Protocol and Subjects

Figure 2:
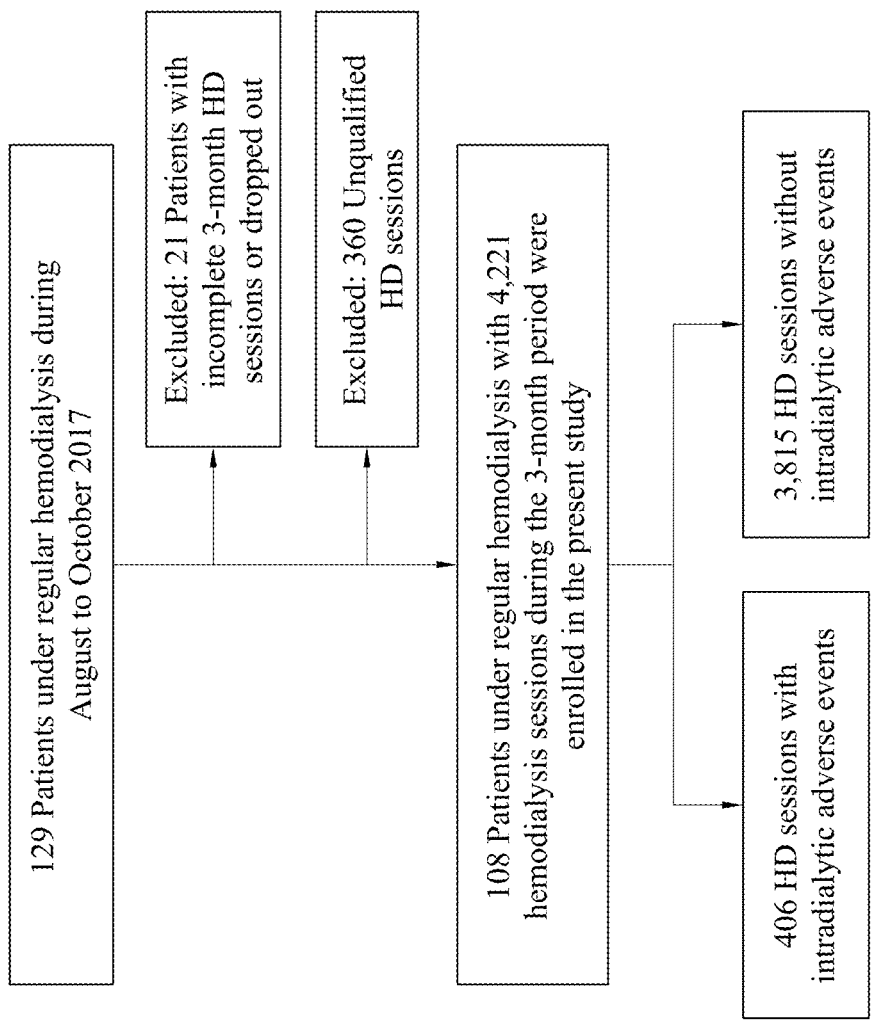
FIG. 2 is a flow chart illustrating the decision process for selecting patients and HD sessions in accordance with embodiments of the present disclosure.

In a practice where a retrospective observational study took place in a single institution, records of all patients underwent maintenance HD therapy at Changhua Christian Hospital were reviewed. FIG. 2 shows a decision process of how patients and HD sessions are selected for study in accordance with embodiments described herein. For example, during a period of three months, 108 out of 129 eligible patients have completed in this three-month study, and HD sessions from said 108 patients were excluded for the following reasons: (1) session interruption due to dialyzer exchange; (2) more than one interruption per session due to patient urination or defecation; and/or (3) inability of patients to freely express their discomfort during the session. Eventually, a total of 4,221 HD sessions from said 108 patients were used to build machine learning model(s) for predicting intradialytic adverse events, where each patient received either 39 or 40 HD sessions during the 3-month study period.

Dialysis and Physiological Data Collection

In the embodiments described herein, several types of data were collected by the feature extraction module 10 for building machine learning model(s), e.g., demographic information, physiological data, dialysis data and registered intradialytic adverse events. Aforementioned types of data may be collected either via manual (e.g., having medical staff taking measurements) or automatic means (e.g., having the HD machine taking measurements by itself), of which the present disclosure is not limited thereto.

In at least one embodiment, the demographic information may be derived from medical records, and may include information such as age, gender, and years under dialysis treatment, etc. of any arbitrary patient.

In at least one embodiment, the physiological data were measured and recorded approximately every 30 to 60 minutes during each HD session (approximately four hours for each HD session) of the enrolled patients.

In at least one embodiment, the dialysis data were collected from the HD machine during each HD session of the enrolled patients. An example of HD machine readouts related to the dialysis data are shown in Table 1 below.

TABLE 1

List of HD machine readouts

| Parameter | Unit | Abbreviation |
|---|---|---|
| Systolic blood pressure | mmHg | SBP |
| Diastolic blood pressure | mmHg | DBP |
| Pulse rate | beat/min | PR |
| Blood flow | mL/min | BF |
| Venous pressure | mmHg | VP |
| Transmembranous pressure | mmHg | TMP |
| Dialysate conductivity | % | |
| Dialysate temperature | ° C. | |
| Ultrafiltration rate | L/hour | UF rate |
| Ultrafiltration volume | L | UF volume |

In at least one embodiment, registered intradialytic adverse events were documented according to physiological data being measured or patient complaints. An example of intradialytic adverse events being documented from enrolled patients are shown in Table 2 below.

TABLE 2

List of intradialytic adverse events and occurrence count

| Adverse event | Episodes, n |
|---|---|
| Muscle cramps | 138 |
| Blood pressure elevation | 108 |
| Low blood pressure | 64 |
| Miscellaneous | 45 |
| Headache | 28 |
| Lightheadedness | 26 |
| Chest tightness | 23 |
| Vascular access thrombosis | 23 |
| Cold sweating | 22 |
| Nausea/vomiting | 12 |
| Fever | 10 |
| Tachycardia | 10 |
| Dyspnea | 8 |
| Hoarseness | 8 |
| Chills | 5 |
| Leg pain | 5 |
| Low back pain | 5 |

TABLE 2-continued

List of intradialytic adverse events and occurrence count

| Adverse event | Episodes, n |
|---|---|
| Shoulder pain | 5 |
| Altered mental status | 4 |
| Chest discomfort | 3 |
| Numb hands | 3 |
| Tinnitus | 3 |
| Vascular access occlusion | 3 |
| Abdominal pain | 2 |
| Hypersomnia | 1 |
| Palpitation | 1 |
| Pruritus | 1 |

Referring to Table 3-1 to 3-2 below, an example of data collected by the feature extraction module 10 is disclosed. In the practice where a total of 4,221 HD sessions from 108 patients was under study, the feature extraction module 10 collected a data set $HD_i$ consisted of a plurality of records $\{Y_{j,k}, T_k\}$ for each HD session i (i=1 to 4,221), where j (see Table 3-1, ranges 1 to 9) is the index for categories of data from dialysis and physiological measurements, k is the index of time when a measurement is taken place, and $Y_{j,k}$ is the value of the measurement j at time $T_k$. Referring to the records marked with thick boundaries in Table 3, it shows all types of data point $Y_{j,4}$ being measured at timestamp of "$T_4$=9:35:44" (i.e., $\{Y_{j,4}, T_4\}$). According to the manufacturer default setting, the dialysis data and/or the physiological data are typically recorded from the HD machine automatically once the value of venous pressure (VP) or transmembranous pressure (TMP) alters and becomes different from the last measurement at $T=T_{k-1}$. Therefore, the time interval $T_k$-$T_{k-1}$ between any two consecutive records may not be equal.

TABLE 3-1

Exemplifying data collected from HD sessions of a patient

| Time Stamp Tk | SBP $Y_{1,k}$ | DBP $Y_{2,k}$ | Pulse Pressure $Y_{3,k}$ | PR $Y_{4,k}$ | BF $Y_{5,k}$ | VP $Y_{6,k}$ | TMP $Y_{7,k}$ | UF Rate $Y_{8,k}$ | UF Volume $Y_{9,k}$ |
|---|---|---|---|---|---|---|---|---|---|
| $T_1$ = 8:12:44 | | | | | 248 | 100 | 76 | 0.9 | 0.013 |
| $T_2$ = 8:33:37 | 152 | 74 | 78 | 72 | 248 | 103 | 39 | 0.9 | 0.315 |
| $T_3$ = 9:04:55 | | | | | 248 | 94 | 37 | 0.9 | 0.782 |
| $T_4$ = 9:35:44 | 149 | 75 | 74 | 74 | 248 | 100 | 39 | 0.9 | 1.245 |
| $T_5$ = 9:43:29 | | | | | 251 | 100 | 38 | 0.9 | 1.365 |
| $T_6$ = 10:14:18 | 134 | 69 | 65 | 66 | 248 | 109 | 41 | 0.9 | 1.823 |
| $T_7$ = 10:45:05 | | | | | 248 | 112 | 44 | 0.9 | 2.29 |
| $T_8$ = 11:15:52 | 96 | 31 | 65 | 77 | 248 | 118 | 43 | 0.9 | 2.749 |
| $T_9$ = 11:30:25 | | | | | 248 | 127 | 37 | 0.093 | 2.966 |
| $T_{10}$ = 11:30:48 | | | | | 251 | 127 | 35 | 0.193 | 2.966 |
| $T_{11}$ = 11:31:00 | 93 | 48 | 45 | 78 | 251 | 127 | 35 | 0.193 | 2.966 |

TABLE 3-2

Exemplifying data collected from HD sessions of a patient

| Gender (Male = 1, Female = 0) $Y_{10}$ | Age $Y_{11}$ | Vintage of HD $Y_{12}$ | Predialytic Weight $Y_{13}$ |
|---|---|---|---|
| 0 | 61 | 18 | 64 |

Continuing to Table 3-2, each data set $HD_i$ also includes additional time-invariant patient-specific information $Y_j$ (j=10 to 13), which represents information of age, gender, vintage of HD, and predialytic weight of the patient during the corresponding HD session respectively.

It should be understood that when the system is ready for practical use (e.g., a fully trained machine learning model is developed), the data set $HD_i$ described in Table 3 may be directly utilized for feature extraction and intradialytic adverse event prediction. However, an intradialytic adverse event may also be registered to the data set $HD_i$ to act as a training data for building machine learning model.

Feature Extraction

After data collection, the feature extraction module 10 proceeded to extract data from the data set $HD_i$ from HD sessions as features for analysis. In the embodiments described herein, feature extraction is ideally performed using an AWK program, but any suitable program or application may be utilized, of which the present disclosure is not limited thereto.

To avoid artifacts at the beginning of the data set $HD_i$ due to different procedures on how dialysis is set up and started in each HD session, the first data points $Y_{j,1}$ (i.e., record $\{Y_{j,1}, T_1\}$) at the beginning of each data set $HD_i$ will be excluded if the blood flow rate (i.e., data points $Y_{5,k}$) varied between timestamps $T_1$ and $T_2$. Records $\{Y_{j,k}, T_k\}$ at any given timestamp $T_k$ will also be excluded if the blood flow rate (i.e., data points $Y_{5,k}$) is equal to or below zero due to dialysis interruption (e.g., dialyzer exchange or patient urination/defecation). An entire HD session (the complete data set $HD_i$) will be excluded from feature extraction if the HD session is interrupted more than once.

For training data, a complete collection of records $\{Y_{j,k}, T_k\}$ of a data set $HD_i$ from an HD session will be included for feature extraction if no intradialytic adverse event (e.g., any one of adverse events listed in Table 2 as described above) is registered for said HD session. On the other hand, for an HD session registered with intradialytic adverse events, only records $\{Y_{j,k}, T_k\}$ of the corresponding data set $HD_i$ preceding the first occurrence of an adverse event will be included for feature extraction, meaning that the duration of this HD session is less than 4 hours.

Since time interval between two adjacent records $\{Y_{j,k}, T_k\}$ and duration of HD sessions vary, regression analysis is deemed challenging, and temporal features of the measured variables are needed to include in the analysis for classification. To this end, the feature extraction module 10 derived mean, standard deviation of the mean, and coefficient of variance, as well as the slope and R square of linear regression from the records $\{Y_{j,k}, T_k\}$ of dialysis and physiological measurements as features for analysis. Further, maximum, minimum, and mean of change rate (first-order derivative), as well as second-order derivative of venous pressure (VP) and transmembranous pressure (TMP) were also derived by the feature extraction module 10 as features for analysis.

Referring to Tables 4 and 5 below, an example of features extracted by the feature extraction module 10 from an HD session is disclosed. For example, a total of 84 features $\{X_h\}$ (h=1 to 84, referring to feature numbers denoted as shown, where "#" represents "number") was extracted, including those from the raw measurements and those derived from the temporal aspect of the data set $HD_i$ as discussed above. However, based on content of the data set $HD_i$ in practice, the total of features may be more than or less than 84, of which the present disclosure is not limited thereto.

30 for prediction of an intradialytic adverse event. As discussed above, records $\{Y_{j,k}, T_k\}$ of the data set $HD_i$ were recorded once values of venous pressure or transmembranous pressure change. Therefore, the value of any measurement at a time $T_p$ between two adjacent measured timestamps, $T_k$ and $T_{k-1}$, can be assigned as $\{Y_{j,k}, T_p\}=\{Y_{j,k}, T_{k-1}\}$. That is, feature extraction of the data set $HD_i$ in an HD session can be terminated at an arbitrary time (e.g., $T_p$) for storage or prediction when the feature extraction module 10 is operating in real time.

Outcome Labeling for Model Building

During training, outcomes related to HD sessions may be labeled first before the corresponding data sets $HD_i$ and/or

TABLE 4

Exemplifying features extracted from the data during HD sessions of patients

| | | | | Operator Feature # | | | | | |
|---|---|---|---|---|---|---|---|---|---|
| Parameter X | None | Maximum | Minimum | Mean value | Standard deviation of mean | Coefficient of variance | Slop of linear regression | R-squared of linear regression | Mean of (1/time interval)$^A$ |
| Gender | 1 | | | | | | | | |
| Age | 2 | | | | | | | | |
| Predialytic body weight | 3 | | | | | | | | |
| Vintage of hemodialysis | 84 | | | | | | | | |
| Systolic blood pressure | | 4 | 5 | 6 | 7 | | 8 | 9 | |
| Diastolic blood pressure | | 10 | 11 | 12 | 13 | | 14 | 15 | |
| Pulse pressure | | 16 | 17 | 18 | 19 | | 20 | 21 | |
| Pulse rate | | 22 | 23 | 24 | 25 | | 26 | 27 | |
| Blood flow rate | | 28 | 29 | 30 | 31 | | 32 | 33 | |
| Venous pressure | | 34 | 35 | 36 | 37 | 38 | 39 | 40 | 41 |
| Transmembranous pressure | | 52 | 53 | 54 | 55 | 56 | 57 | 58 | 59 |
| Ultrafiltration rate | | 70 | 71 | 72 | 73 | | 74 | 75 | |
| Ultrafiltration volume | | 78 | 79 | 80 | 81 | | 82 | 83 | |

TABLE 5

Exemplifying features extracted from the data during HD sessions of patients

| | | | | | | | Operator Feature # | | | | | |
|---|---|---|---|---|---|---|---|---|---|---|---|---|
| Parameter X | Max. of change rate$^B$ K | Mini. of K | Mean of K | Max. of $K_i - K_{i-1}$ | Mini. of $K_i - K_{i-1}$ | Mean of $K_i - K_{i-1}$ | Max. of change $\Delta X_i^C$ | Mini. of $\Delta X_i$ | Mean of $\Delta X_i$ | Mean* of $\Delta X_i^D$ | Number of times that X changed | Mean of $|\Delta X_i|$ |
| Venous pressure | 42 | 43 | 44 | 45 | 46 | 47 | 48 | 49 | 50 | 51 | | |
| Transmembranous pressure | 60 | 61 | 62 | 63 | 64 | 65 | 66 | 67 | 68 | 69 | | |
| Ultrafiltration rate | | | | | | | | | | | 76 | 77 |

Note:
A: time interval ≡ $T_i - T_{i-1}$, i = 1~n
B: $K_i = \Delta X_i/(T_i - T_{i-1}) = (X_i - X_{i-1})/(T_i - T_{i-1})$
C: $\Delta X_i \equiv X_i - X_{i-1}$
D: mean* is weighted by duration and then divided by total recording time,
$\Sigma((X_i - X_{i-1}) \times (T_i - T_{i-1}))/\Sigma(T_i - T_{i-1}) = \Sigma((X_i - X_{i-1}) \times (T_i - T_{i-1}))/(T_n - T_0)$ After feature extraction, the feature extraction module 10 stored the extracted feature(s) to the data storage module 20 for later use (e.g., for building a machine learning model), or directly send to the model building and optimization module their extracted features are used for model building. For example, among the 4,221 HD sessions being studied, HD sessions with one or more than one adverse event were labeled as 1, and HD sessions with no adverse event were labeled as 0. A negative control set may also be set by randomly relabel said 4,221 HD sessions regardless of their true outcome while keeping the same 0 to 1 ratio as an experimental set.

After outcome labeling, the model building and optimization module 30 performed its building process for machine learning model(s), including: (1) building a two-class classification model (e.g., using algorithms such as ensemble or perceptron), which outputs label 0 or 1 for a given data set HDi upon input; and (2) evaluating said two-class classification model via a four-fold cross-validation (e.g., utilizing cloud computing platform AZURE® by MICROSOFT INC.). For each machine learning model, at least three repeats of said building process were performed by introducing different random numbers for each model building.

Selection for Top Performance Features

In addition to labeling of outcomes, machine learning models may also be built on selected key features from a total of 84 features. For example, the model building and optimization module 30 was also configured to implement algorithms to select key features related to occurrence of intradialytic adverse events during building of the machine learning model(s). By determining key features for model building, computing load may be effectively reduced without losing prediction accuracy. Further, key features may act as the reference basis for adjusting parameters of HD machines after a prediction of intradialytic adverse events was made by the machine learning model based on said key features.

For example, to pinpoint which features are more important than others in predicting targeted intradialytic adverse event(s), key features (from a total of 84 features) may be selected and used for model building of the model building and optimization module 30, such that differences between predicting outcomes from those machine learning models built with selected key features and those built with a total of 84 features may be compared. From here, the selection of key features may be performed using computing program such as MATLAB® by MATHWORKS INC., but any suitable program or application may be utilized and not be restrictive to the scope of the present disclosure. Then, the selected key features may be used to build the machine learning model as discussed above (e.g., building a two-class classification model using ensemble random under-sampling boosted trees and evaluating by four-fold cross-validation). Next, a score may be given to the built machine learning model by summing up the percentages of true positives and true negatives from its predicting outcome, which was used for comparison at a later stage.

The process of key feature selection is further detailed herein. First, a first set of machine learning models were built by using a single feature from the 84 features once at a time, and each of the first set of machine learning models was given a score based on its predicting outcome (which is based on percentages of true positives and true negatives). Then, top two-feature combinations were selected from a two-feature combination pool to build a second set of machine learning models, where the two-feature combination pool was established by combining the top feature selected by scores of the first set of machine learning models in the previous step (e.g., the feature that contributes the machine learning model of the highest score) with each of the remaining 83 features. Next, the two-feature combinations selected for the second set of machine learning models that resulted in scores higher than the top score of the first set of machine learning models were kept for the next step.

Likewise, the top three-feature combinations can be selected from a three-feature combination pool to build a third set of machine learning models, where the three-feature combination pool is established by combining the top two-feature combinations selected by scores of the second set of machine learning models (e.g., the top two-feature combinations that contributes the machine learning models of the highest scores) with each of the remaining 82 features, and the three-feature combinations selected for the third set of machine learning models that resulted in scores higher than the top score of the second set of machine learning models were kept for another next step. This procedure was repeated until the top 20-feature combinations were selected, where the features most frequently appeared in these 20-feature combinations were defined as key features.

Results

Demographic Characteristics of the Study Participants

Table 6 below shows a chart summarizing the characteristics of said 108 patients enrolled in the study in accordance with embodiments described herein. For example, among said 108 patients, the mean age is 63.6 years; 60 (55.6%) patients are male; mean vintage of HD is 7.7 years; 47 (43.5%) patients have diabetes mellitus; 69 (63.9%) patients have hypertension; 11 (10.2%) patients have coronary artery disease; 12 (11.1%) patients have congestive heart failure; 7 (6.5%) patients have history of stroke; 3 (2.8%) patients have chronic obstructive pulmonary disease; 2 (1.9%) patients have peripheral vascular disease; and 2 (1.9%) patients have malignancy.

TABLE 6

| Demographic characteristics of the enrolled patients (n = 108) | |
|---|---|
| Age (year) | 63.6 ± 11.1 |
| Male gender (n; %) | 60; 55.6 |
| Vintage of HD (year) | 7.7 ± 6.2 |
| Comorbidities | |
| Diabetes mellitus (n; %) | 47; 43.5 |
| Hypertension (n; %) | 69; 63.9 |
| Coronary artery disease (n; %) | 11; 10.2 |
| Congestive heart failure (n; %) | 12; 11.1 |
| Prior stroke (n; %) | 7; 6.5 |
| Chronic obstructive pulmonary disease (n; %) | 3; 2.8 |
| Peripheral vascular disease (n; %) | 2; 1.9 |
| Malignancy (n; %) | 2; 1.9 |

Data were presented as mean ± SD or percentage as appropriate.

Moreover, in accordance with occurrences of intradialytic adverse events (referring to Table 2) documented from these 108 patients, 4 HD sessions have more than three intradialytic adverse events; 19 HD sessions have three adverse events; 106 HD sessions have two adverse events; and 276 HD sessions have a single adverse event. Altogether, there are 406 HD sessions with adverse events out of 4,221 total HD sessions.

Performance of the Model for Prediction

To increase the outcome 1 to 0 ratios (i.e., HD sessions with an adverse event is labeled as 1, and HD sessions without an adverse event is labeled as 0), the 27 adverse events listed in Table 2 were categorized into three groups for building machine learning models. The first group corresponded to all the intradialytic adverse events with exclusion of blood pressure elevation, vascular access occlusion, and vascular access thrombosis, where a total of 323 HD sessions was assigned to this group (Group 1). The second group corresponded to the intradialytic adverse events including muscle cramps, where 138 HD sessions were assigned to this group (Group 2). The third group corresponded to the intradialytic adverse events including blood pressure elevation, where 108 HD sessions were assigned to this group (Group 3).

Group 1: All Events Except Blood Pressure Elevation

Figure 3A:
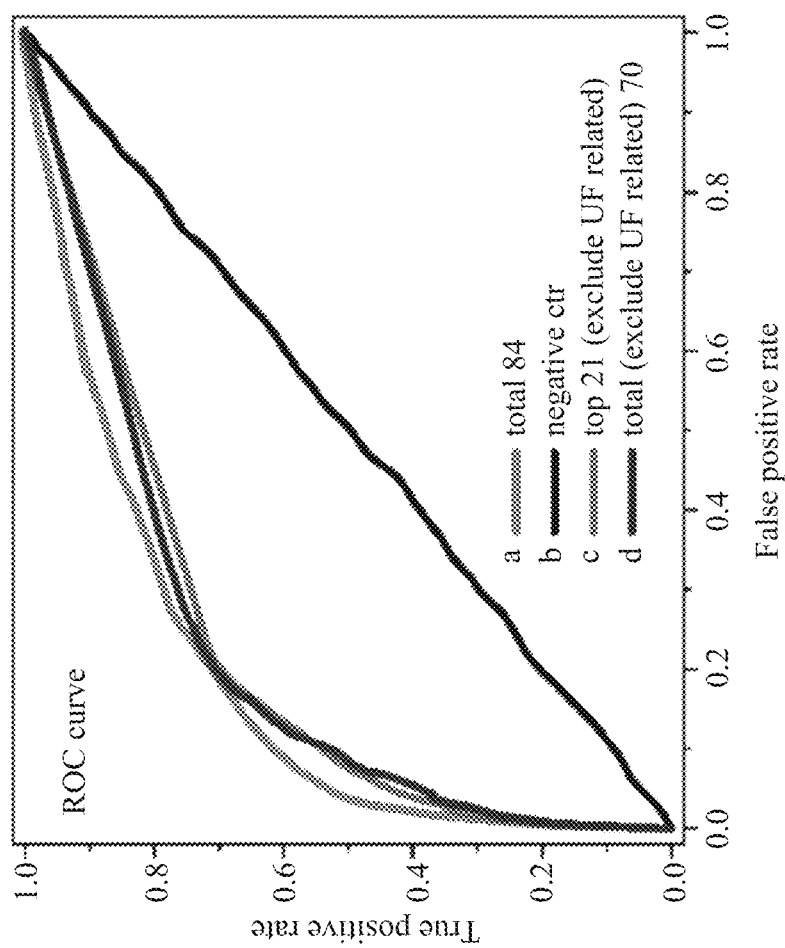
FIGS. 3A and 3B are diagrams illustrating performance of machine learning models for predicting adverse events belonging to Group 1 in accordance with embodiments of the present disclosure; ctr: control; f72, f76, f77, f78, f82: feature nos. indicated in Tables 4 and 5; ave. Δ(UF rate): the mean value of ultrafiltration rate changes.
Figure 3B:
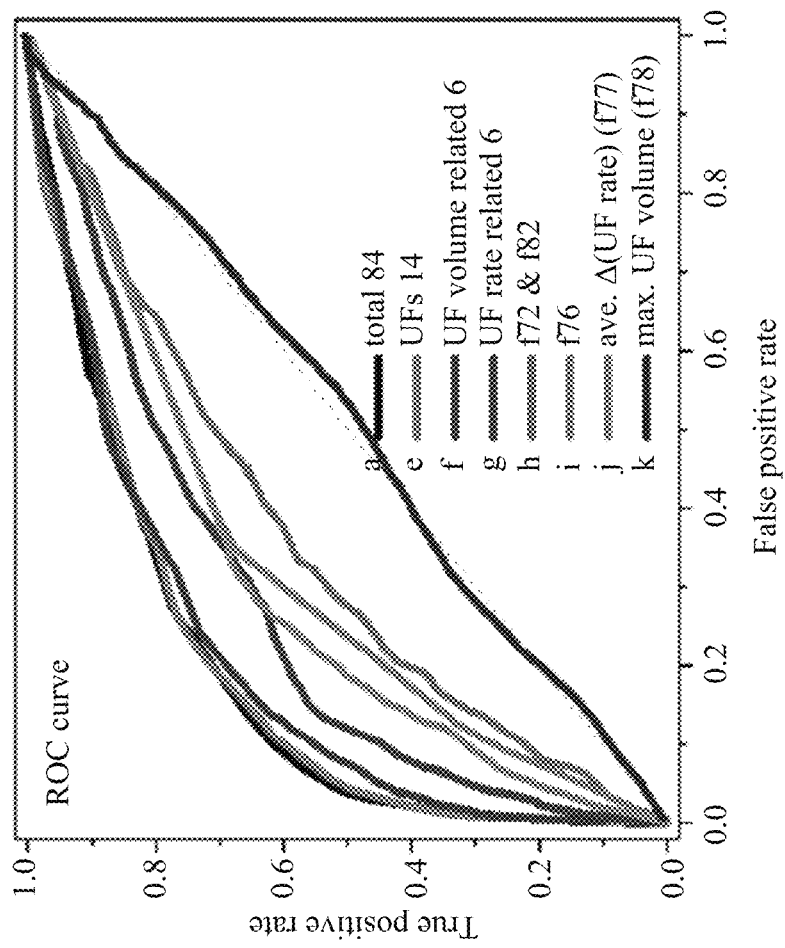

FIGS. 3A and 3B and Table 7 describe performance of machine learning models for predicting adverse events belonging to Group 1, where curves a-k represents machine learning models built by using different combination of features. In this scenario, a two-class averaged perceptron was used for model building with a learning rate of 20 and maximal iterations of 20.

volume recorded at the last time point, has an AUC of 0.48 and an F1 score of 0.15, which are similar to the results of the negative control. On the other hand, the model built by the mean value of ultrafiltration rate changes during HD sessions has an AUC of 0.70 and an F1 score of 0.28. Combining two ultrafiltration-related features (curve h) also fails to predict adverse events. After up to six ultrafiltration volume-related features (features 78-83, referring to curve f) were used for prediction, the AUC increased from 0.48 to 0.82, and the F1 score increased from 0.15 to 0.46. The model with 14 ultrafiltration features (features 70-83, referring to curve e) has an AUC of 0.83 and an F1 score of 0.52.

Next, the 21 features that most frequently appeared in the 20-feature combinations were selected for the evaluation

TABLE 7

Performance of machine learning models for predicting adverse events belonging to Group 1

| | a<br>All features | b<br>All with outcome randomly labeled | c<br>Top features without UF related features | d<br>All without UF related features | e<br>UF related features | f<br>UF volume related features | g<br>UF rate related features | h<br>Two UF related features | i | j | k |
|---|---|---|---|---|---|---|---|---|---|---|---|
| | | | | | | | | | | Single UF related features | |
| Feature included | 1-84 | 1-84 | 2, 5, 6, 8, 11, 14, 17, 20, 21, 26, 29, 31, 36, 47-49, 50-52, 57, 59 | 1-69, 84 | 70-83 | 78-83 | 70-77 | 72, 82 | 76 | 77 | 78 |
| Number of features used | 84 | 84 | 21 | 70 | 14 | 6 | 8 | 2 | | 1 | |
| AUC | 0.83 | 0.50 | 0.82 | 0.81 | 0.83 | 0.82 | 0.75 | 0.65 | 0.69 | 0.70 | 0.48 |
| F1 score | 0.53 | 0.15 | 0.45 | 0.45 | 0.52 | 0.46 | 0.36 | 0.22 | 0.25 | 0.28 | 0.15 |

For the 84-feature model (curve a), the mean area under the curve (AUC) is 0.83 and has a standard deviation (SD) of 0.03, with an F1 score of 0.53, sensitivity of 0.53, and specificity of 0.96. When compared with the negative control (curve b), where a mean AUC is 0.50 and has an SD of 0.04, with an F1 score of 0.15), the 84-feature model of the two-class averaged perceptron can predict adverse events plausibly. Other algorithms were also tested for the prediction. For example, the mean AUC obtained by two-class support vector machines (SVM) is 0.83 (SD 0.02), with an F1 score of 0.55, sensitivity of 0.53, and specificity of 0.96. The results were similar to those obtained by the averaged perceptron. Compared to averaged perceptron and SVM algorithms, two-class logistic regression and decision forest did not predict the adverse events well. The mean AUC obtained by logistic regression is 0.82 (SD 0.02), with an F1 score of 0.48, and the mean AUC obtained by decision forest is 0.83 (SD 0.02), with an F1 score of 0.46. Additionally, interpatient partition (a mean AUC is 0.83, SD 0.03 with a mean F1 score of 0.53, SD 0.02) and interpatient partition (a mean AUC is 0.82, SD 0.04 with a mean F1 score of 0.50, SD 0.06) for sampling do not show significant difference in prediction.

Ultrafiltration rate and ultrafiltration volume are relevant parameters for HD. However, performances of models herein indicated that employing a single feature, such as the maximal value of ultrafiltration volume (feature 78, referring to curve k) or the mean value of ultrafiltration rate changes (feature 77, referring to curve j), cannot predict adverse events properly. The model built by the maximal value of ultrafiltration volume, defined as the ultrafiltration (curve c). The two-class averaged perceptron model based on these top 21 performance features but skipping ultrafiltration-related features shows a mean AUC of 0.82 (SD 0.02) and an F1 score of 0.45. However, increasing one or two features for the model do not enhance the prediction significantly (e.g., the 23 top features model merely results in a mean AUC of 0.82, SD 0.02 and an F1 score of 0.46). When compared with the model based on all features but excluding ultrafiltration-related features (referring to curve d, where 70 features are used, and an AUC is 0.81, an F1 score is 0.45), the results of the 21 top features model (without ultrafiltration-related features) demonstrated that a quarter of the total 84 features is sufficient to predict adverse events.

To be exact, the 21 features selected from the total 84 features in this case are age, maximum transmembranous pressure, minimum systolic blood pressure (SBP), minimum diastolic blood pressure (DBP), minimum pulse pressure, minimum blood flow rate, mean SBP, mean venous pressure, mean transmembranous pressure, slope of linear regression of SBP, slope of linear regression of DBP, slope of linear regression of pulse pressure, slope of linear regression of pulse rate, slope of linear regression of transmembranous pressure, standard deviation of the mean of blood flow rate, R-squared of linear regression of pulse pressure, and related parameters to the second-order derivative of venous pressure (referring to features 2, 5, 6, 8, 11, 14, 17, 20, 21, 26, 29, 31, 36, 47-52, 57, and 59 listed in Tables 4 and 5).

Group 2: Muscle Cramps

Figure 4:
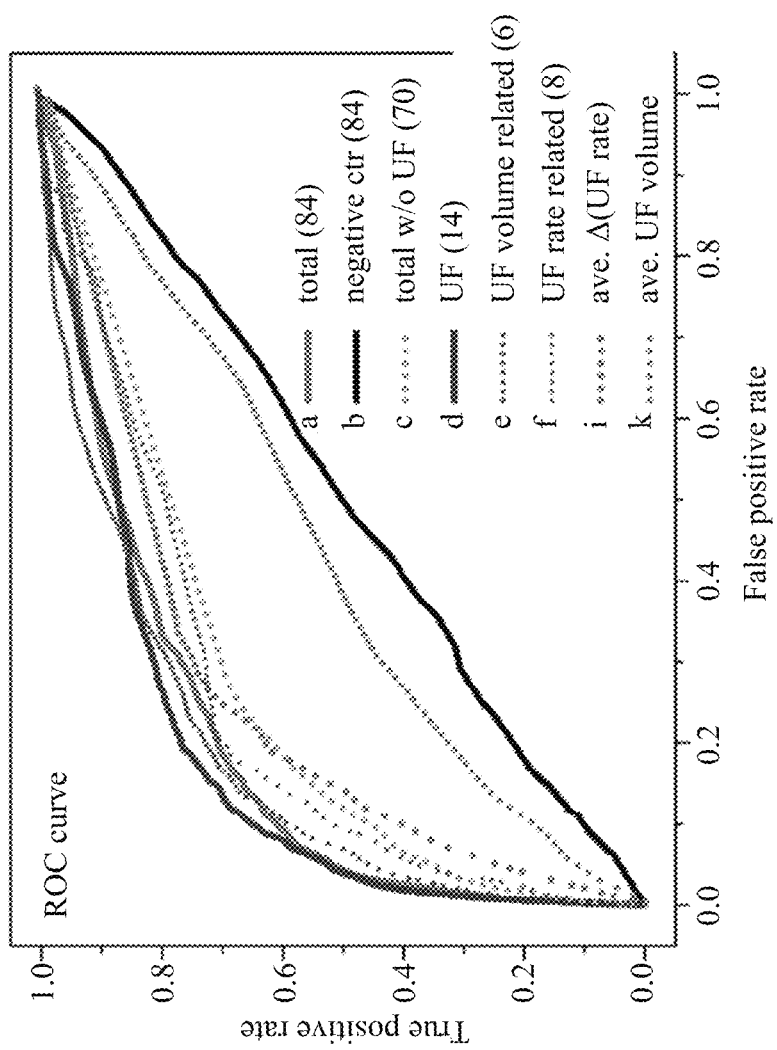
FIG. 4 is a diagram illustrating performance of machine learning models for predicting adverse events belonging to Group 2 in accordance with embodiments of the present disclosure; ctr: control; ave. Δ(UF rate): the mean value of ultrafiltration rate changes; ave. UF volume: the mean value of ultrafiltration volume.

FIG. 4 and Table 8 describe performance of machine learning models for predicting adverse events belonging to Group 2, where curves a to k represent machine learning models built by using different combinations of features.

TABLE 8

Performance of machine learning models for predicting adverse events belonging to Group 2

| | a All features | b All with outcome randomly labeled | c All without UF related features | d UF related features | e UF volume related features | f UF rate related features | i | j | k |
|---|---|---|---|---|---|---|---|---|---|
| | | | | | | | \multicolumn{3}{c}{Single UF related features} | | |
| Features included | 1-84 | 1-84 | 1-69, 84 | 70-83 | 78-83 | 70-77 | 77 | 72 | 80 |
| Number of features used | 84 | 84 | 70 | 14 | 6 | 8 | | 1 | |
| AUC | 0.82 | 0.49 | 0.79 | 0.85 | 0.84 | 0.79 | 0.76 | 0.70 | 0.58 |
| F1 score | 0.42 | 0.07 | 0.30 | 0.45 | 0.37 | 0.29 | 0.22 | 0.16 | 0.08 |

As seen in FIG. 4 and Table 8, the model based on 14 ultrafiltration-related features (referring to curve d) has a mean AUC of 0.85 (SD 0.04) and an F1 score of 0.45 for predicting the occurrence of muscle cramps, and the result is similar to that of the 84-feature model (referring to curve a, where it has a mean AUC of 0.82, SD 0.04 and an F1 score of 0.42) and better than that of the model built based on all features but excluding ultrafiltration-related features (referring to curve c, where it has a mean AUC of 0.79, SD 0.04 and an F1 score of 0.30). However, a single ultrafiltration-related feature (referring to curves i and k) cannot predict cramps properly. The combination of two ultrafiltration-related features also fails to predict muscle cramps (referring to curve f, where features 70 to 77 are included, and has an AUC of 0.79 and an F1 score of 0.29; or curve e, where features 78 to 83 are included, and has an AUC of 0.84 and an F1 score of 0.37). The results demonstrated that ultrafiltration-related features contribute more than other features to the prediction of muscle cramps.

Group 3: Blood Pressure Elevation

Figure 5:
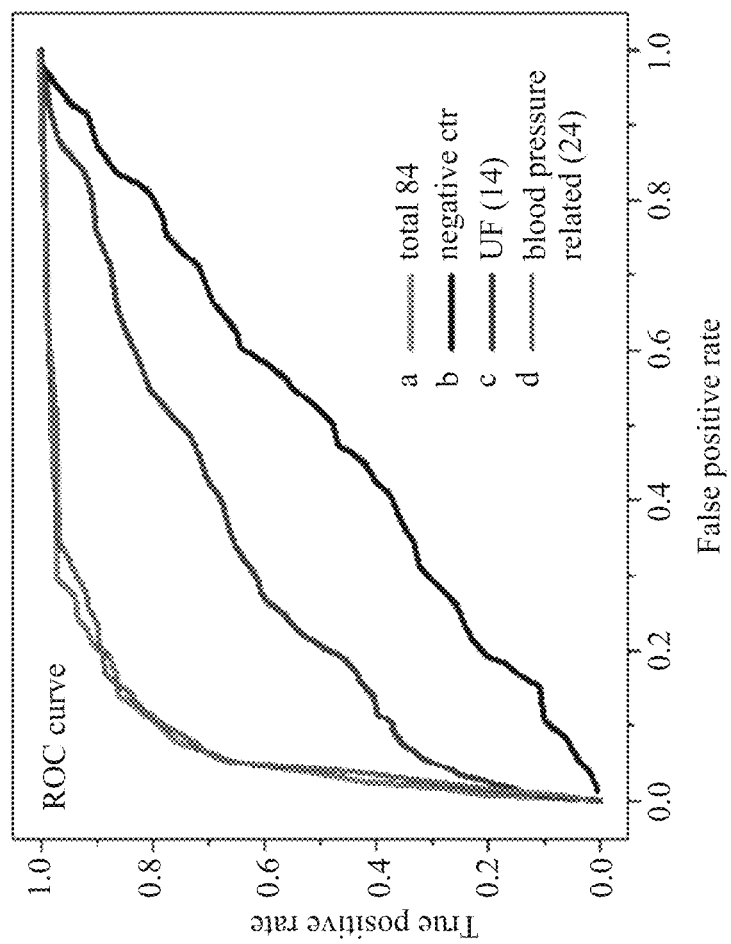
FIG. 5 is a diagram illustrating performance of machine learning models for predicting adverse events belonging to Group 3 in accordance with embodiments of the present disclosure; ctr: control.

FIG. 5 and Table 9 describe performance of machine learning models for predicting adverse events belonging to Group 3, where curves a to d represent machine learning models built by using different combinations of features.

TABLE 9

Performance of machine learning models for predicting adverse events belonging to Group 3

| | a All features | b All with outcome randomly labeled | c UF related features | d Features related to blood pressure |
|---|---|---|---|---|
| Features included | 1-84 | 1-84 | 70-83 | 4-27 |
| Number of features used | 84 | 84 | 14 | 24 |
| AUC | 0.93 | 0.53 | 0.72 | 0.92 |
| F1 score | 0.41 | 0.08 | 0.22 | 0.38 |

As seen in FIG. 5 and Table 9, the model based on a total of 84 features (referring to curve a) has a mean AUC of 0.93 (SD 0.02) and an F1 score of 0.41 for predicting the occurrence of hypertension. When compared with the model built based on 14 ultrafiltration-related features (referring to curve c, where an AUC is 0.72 and an F1 score is 0.22), the results demonstrated that ultrafiltration parameters fail to play important roles in predicting intradialytic hypertension. Even though the model based on 24 blood pressure-related features (referring to curve d, where an AUC is 0.92, SD is 0.03 and an F1 score is 0.38) has an AUC higher than 0.9, features other than blood pressure can further contribute to an additional improvement in the F1 score.

Consistency of the Predicted Probabilities of Adverse Events Over Time

Figure 6:
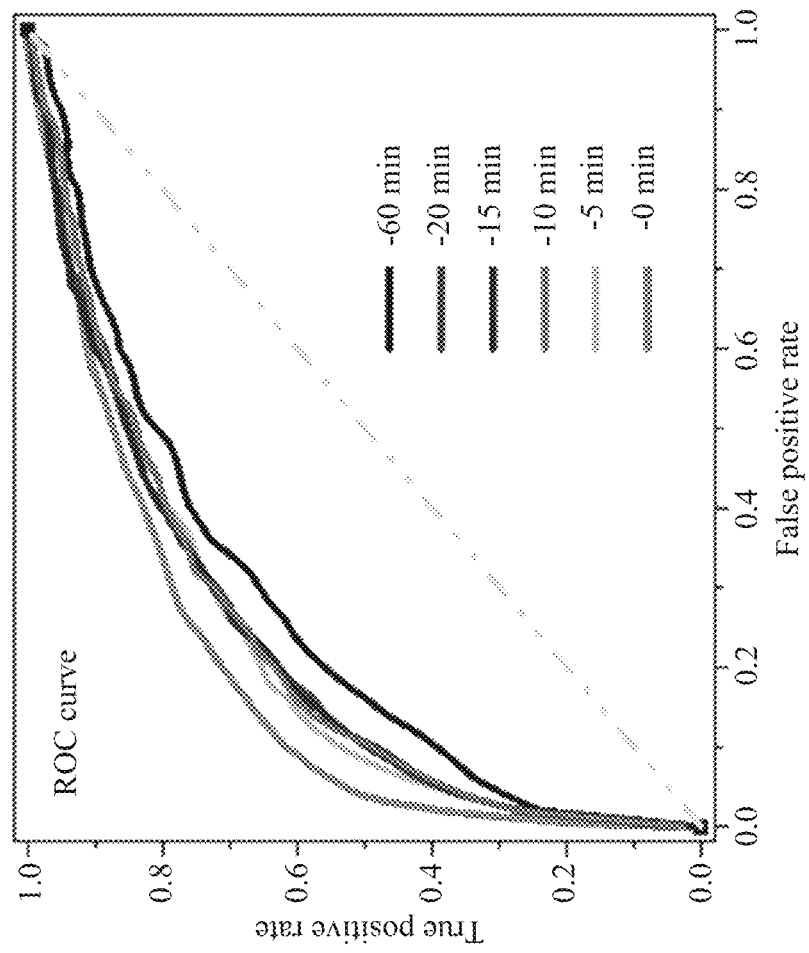
FIGS. 6 and 7 are diagrams illustrating consistency of predicted probabilities of adverse events over time based on machine learning models in accordance with embodiments of the present disclosure.
Figure 7:
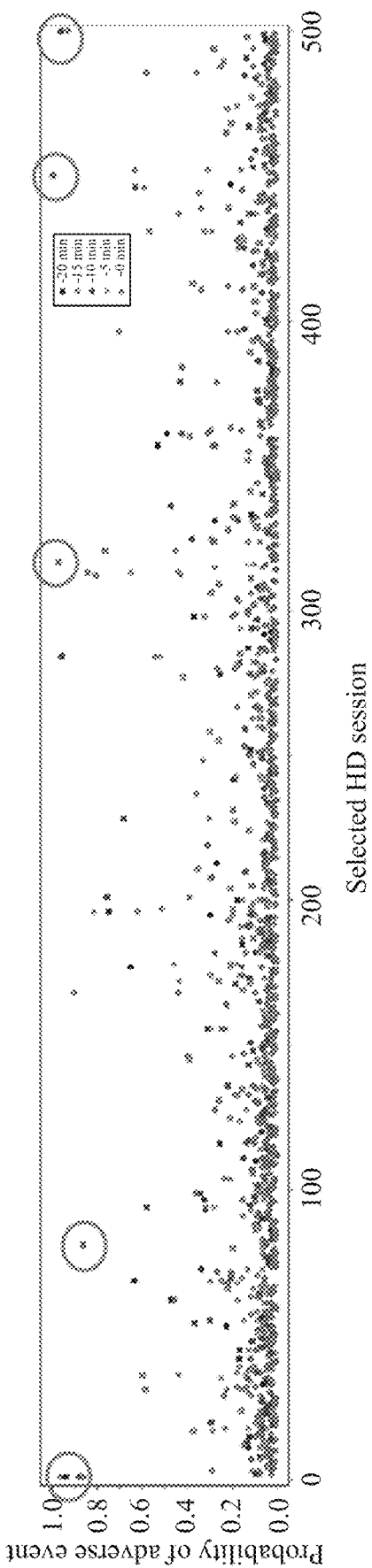

FIGS. 6 and 7 and Table 10 describe performances of machine learning model(s) for predicting intradialytic adverse events based on time series features, where curves denoted as 0, 5, 10, 15, 20 and 60 minutes represent the prediction ability of said machine learning model(s) at denoted time before occurrence of any of the intradialytic adverse events.

TABLE 10

Consistency of predicted probabilities of adverse events over time

| Time before the event | True positive | False positive | False negative | True negative | AUC | F1 score |
|---|---|---|---|---|---|---|
| 0 min | 168 | 131 | 155 | 3684 | 0.83 | 0.53 |
| 5 min | 149 | 221 | 174 | 3594 | 0.80 | 0.43 |
| 10 min | 135 | 207 | 188 | 3608 | 0.79 | 0.41 |
| 15 min | 124 | 143 | 199 | 3672 | 0.80 | 0.42 |
| 20 min | 134 | 179 | 189 | 3636 | 0.79 | 0.42 |
| 60 min | 102 | 126 | 221 | 3689 | 0.75 | 0.37 |

In the embodiments described herein, time series features were collected throughout the HD sessions: from the beginning of the HD sessions to the time point right before the documented adverse event or right before the end of the HD session (i.e., no adverse event documented). In this case, the end of feature collection is defined as 0 minutes if this ending time point is right before the occurrence of the documented adverse event. In addition to 0 minutes, the cutoff ending time points of feature collection is also set as 5, 10, 15, 20, and 60 minutes before the occurrence of the adverse event to evaluate the prediction accuracy.

As seen in FIG. 6 and Table 10, machine learning models for predicting all intradialytic adverse events, except blood pressure elevation, showed that features of the 0-minute cutoff led to the best AUC and F1 score (referring to curve 0 min, where an AUC is 0.83 and an F1 score is 0.53)

compared to those learned from the features of earlier cutoff time points, even though AUC scores from the features of the cutoff ending time points 5, 10, 15, and 20 minutes before the documented adverse event or before the end of HD sessions without an adverse event are about 0.80 and their F1 scores are all lower than 0.5. This result suggests that while the information embedded in the 20-minute time window before the index adverse event is valuable, the information embedded in the 5-minute time window before the index adverse event is more influential for event prediction.

Referring to FIG. 7, in order to further understand the cutoff ending time point dependence of prediction accuracy, 500 HD sessions were randomly selected to compare the prediction probabilities of adverse events obtained from 84 features with cutoff ending time points of 0, 5, 10, 15, and 20 minutes before the documented adverse event. As indicated by the circled data points, there were five HD sessions possess strong consistency in the predicted probabilities of adverse events using extracted features based on different cutoff ending time points, and adverse events occurred in these five HD sessions. Since there should be approximately 40 HD sessions developing adverse events among 500 randomly selected HD sessions, the results suggest that at least one-tenth of HD sessions with adverse events can be sighted as early as 20 minutes in advance and can be further confirmed by real-time machine learning using features from subsequent cutoff ending time points.

Even though none of the 84 features contained explicit time series information, the linear and differential analysis that feature extraction employed may be affected by the length of HD sessions. Therefore, the HD sessions with no adverse events (negative ones) were truncated, and their prediction results were compared with the prediction results of the untruncated ones. Since the average length of HD sessions with adverse events (positive ones) is 3.3 hours, negative HD sessions were truncated and randomly assigned with endpoints ($T_{end}$) between 3 and 3.5 hours, and yet the endpoints of positive ones remained unchanged. The records $\{Y_{j,k}, T_k\}$ at endpoint $T_{end}$ is defined according to the same method used for records $\{Y_{j,k}, T_k\}$ at arbitrary time $T_p$. Regarding the results, the mean AUC is 0.89 (SD 0.019), an F1 score is 0.55, sensitivity is 0.52, and specificity is 0.97. Alternately, the AUC is 0.86 with an F1 score of 0.55 when the endpoints were assigned exactly at 3.3 hours. Compared to the original results obtained from the untruncated negative HD sessions with a duration of about 4 hours (an AUC is 0.83, an F1 score is 0.53, sensitivity is 0.53, and specificity is 0.96), the prediction results were better when the endpoints were set earlier. Indeed, the AUC is 0.92, with an F1 score of 0.62, sensitivity of 0.61, and specificity of 0.98, when the endpoints were randomly assigned between 2.5 and 3.5 hours for negative HD sessions.

Contributions and Principal Observations

The findings in accordance with embodiments described herein indicate that algorithms combining linear and differential analysis with two-class classification machine learning predict intradialytic adverse events with high AUCs. When attempting to identify features that contribute the most to predicting all adverse events except hypertension (group 1) from a total of 84 features, only feature 76 and feature 82 among the top 23 features are related to ultrafiltration (the number of times that the ultrafiltration rate changes and the linear regression slope of ultrafiltration volume). After excluding said two ultrafiltration-related features, it is found that the remaining 21 features are sufficient for accurate prediction with good discriminating power, with a slight reduction in the AUC from 0.83 (84 features) to 0.82 (21 features). The model built by 14 ultrafiltration-related features also has a good AUC of 0.83. Therefore, instead of including all 84 features for model building, selecting the top 21 ultrafiltration-unrelated features or integrating a total of 14 ultrafiltration-related features can reduce computing load. The result shown in FIGS. 3A and 3B also suggest that said two clusters of features (curves c and e) may embed similar factors contributing the onset of adverse events.

In the findings in accordance with the embodiments described herein, muscle cramp is an adverse event that occurred most frequently during HD sessions. Muscle cramp is a common adverse event that happens during HD therapy, with a prevalence of 28% among all HD sessions. Muscle cramps result from ischemia of the skeletal muscle tissue, indicating an early sign of hypotension, and it may lead to premature discontinuation of HD sessions. Tissue ischemia during HD is positively related to the ultrafiltration rate. When attempting to identify features that contribute the most to predicting muscle cramp (group 2), the model built by 14 ultrafiltration-related features has an AUC of 0.85 for predicting the occurrence of muscle cramps in this study. When all ultrafiltration-related features (including ultrafiltration rate and ultrafiltration volume) are excluded to test the prediction accuracy, the AUC reduced from 0.82 (84 features) to 0.79 (70 features), indicating that ultrafiltration-related features are relevant but not necessarily required to predict muscle cramps. The results from machine learning revealed that ultrafiltration-independent features contribute to predicting intradialytic muscle cramps as well.

In general, symptomatic hypotension occurs in 20% to 30% of HD sessions. There are two major pathophysiological mechanisms of intradialytic hypotension. First, when plasma fluid removal through ultrafiltration exceeds the rate of plasma refilling into the blood vessels, blood volume reduces. In the meantime, if the cardiovascular and neurohormone systems fail to compensate for the acute vascular volume depletion during ultrafiltration, hypotension occurs. Frequent episodes of intradialytic hypotension may cause reduced ultrafiltration, inadequate "dry weight," increased preload, and impaired heart function that eventually leads to more episodes of hypotension, thus creating a vicious cycle. Meanwhile, frequent intradialytic hypotension disrupts dialysis efficiency and efficacy. It is associated with higher morbidity and mortality, which partly contributes to the reason that cardiovascular disease is the leading cause of morbidity and mortality in HD patients. Existing products have recently developed an intelligent system to predict intradialytic hypotension. However, the machine learning model(s) in accordance with the embodiments described herein not only can further preclude ultrafiltration-related features but also can examine overall intradialytic adverse events instead of only focusing on the hypotensive episode.

For example, as shown in Table 11 below, top 16 features that majorly contribute to predicting muscle cramps are listed, which include patient characteristics, venous pressure, transmembranous pressure, ultrafiltration, blood flow rate, and pulse pressure and others. From here, the minimal value of venous pressure and the mean value of transmembranous pressure are features that with most hits (20 and 17 hits, respectively), and hence are the top two features. These top two features for predicting muscle cramps are derived from HD machine output parameters, indicating that there is a potential to integrate the algorithm discussed herein into the HD machine software to alert clinicians and to adjust HD machine settings in advance. Nevertheless, unlike prediction of adverse events of group 1, for which only two out of the top 23 features were related to ultrafiltration, and eight out of the top 16 features were related to ultrafiltration in terms of predicting muscle cramps, indicating that ultrafiltration-related parameters are relevant factors of muscle cramps.

TABLE 11

Top 16 features for predicting intradialytic muscle cramps

| Top | Hits | Feature# | Feature |
|---|---|---|---|
| 1 | 20 | 35 | Venous pressure-minimum |
| 2 | 17 | 54 | Transmembranous pressure-mean |
| 3 | 15 | 2 | Age |
| 4 | 14 | 84 | The vintage of hemodialysis |
| 5 | 13 | 77 | Ultrafiltration rate change value-mean |
| 6 | 12 | 73 | Ultrafiltration rate change-standard deviation |
| 7 | 12 | 81 | Ultrafiltration volume-standard deviation |
| 8 | 11 | 30 | Blood flow rate-mean |
| 9 | 11 | 82 | Ultrafiltration volume linear regression slope |
| 10 | 10 | 72 | Ultrafiltration rate-mean |
| 11 | 10 | 76 | Ultrafiltration rate-times of change |
| 12 | 9 | 79 | Ultrafiltration volume-minimum |
| 13 | 9 | 80 | Ultrafiltration volume-mean |
| 14 | 8 | 16 | Pulse pressure-maximum |
| 15 | 8 | 19 | Pulse pressure-standard deviation |
| 16 | 8 | 28 | Blood flow rate-maximum |

Among several two-class classification models being built in accordance with embodiments described herein, Bayes point machine, boosted decision tree, and SVM, models built by two-class average perceptron has the best AUC and F1 score. As clinicians are now facing the new era of artificial intelligence, the integration of computer science and dialysis medicine are regarded as the first step to improve HD patients' care quality comprehensively. The embodiments described herein demonstrate the feasibility of this integration. Moreover, integrating machine learning with the HD machine and modifying algorithms in real-time by cloud computing with accumulation of data sets are expected to further enhance prediction performance.

Regarding the advance in time to predict intradialytic adverse events, given that consistency in the predicted probabilities of adverse events using features based on different cutoff ending time points are about one-tenth of HD sessions with prediction of adverse events (referring to FIGS. 6 and 7 and Table 10), it is anticipated that an increase in the number of HD sessions with adverse events for model training can improve imbalanced data and possibly bring forward the timing for the alert. Further, since most of the adverse events took place in second-half HD sessions, it is anticipated that the data sets of second-half HD sessions may be sufficient for prediction if more HD data set are included. Moreover, if more HD sessions with adverse events are recruited, it is anticipated that building models for predicting each one of adverse events respectively may be achievable instead of grouping the events to reduce imbalanced data outcomes.

In the embodiments described herein, a machine learning model of two-class classification is established to predict intradialytic adverse events in quasi-real time, with AUCs higher than 0.8. The consistency in the predicted probabilities of intradialytic adverse events obtained from the features extracted in the ongoing HD process in real time can have the HD session alerted for forthcoming adverse events. Such a methodology implemented with cloud computation can warn clinicians to take necessary actions and adjust the HD machine settings in advance.

The present disclosure has been described with exemplary embodiments to illustrate the features and efficacies of the present disclosure, but not intend to limit the scope of the present disclosure. The present disclosure without departing from the scope of the premise can make various changes and modifications by a person skilled in the art. However, any equivalent change and modification accomplished according to the present disclosure should be considered as being covered in the scope of the present disclosure. The scope of the disclosure should be defined by the appended claims.

What is claimed is:

1. A system for prediction of an intradialytic adverse event, comprising a computer, wherein the computer contains: a feature extraction module configured to collect and process data regarding a hemodialysis session of a patient; and a model building and optimization module configured to build a machine learning model based on the data to predict the intradialytic adverse event during the hemodialysis session, and key features are selected and used to build the machine learning model, wherein, a first set of machine learning models are built by using a single feature from the all features, each of the first set of machine learning models is given a score based on its predicting outcome, then, top two-feature combinations are selected from a two-feature combination pool to build a second set of machine learning models, where the two-feature combination pool is established by combining the top feature selected by scores of the first set of machine learning models in the previous step with each of the remaining features, and then, the two-feature combinations selected for the second set of machine learning models that resulted in scores higher than the top score of the first set of machine learning models are kept for the next step, and then, the top three-feature combinations can be selected from a three-feature combination pool to build a third set of machine learning models, where the three-feature combination pool is established by combining the top two-feature combinations selected by scores of the second set of machine learning models with each of the remaining features, and the three-feature combinations selected for the third set of machine learning models that resulted in scores higher than the top score of the second set of machine learning models are kept for another next step, and this procedure is repeated until predetermined number of top feature combinations are selected and the predetermined number of top feature combinations are defined as the key features.

2. The system of claim 1, wherein the data regarding the hemodialysis session of the patient comprise one or more of demographic information, physiological data, dialysis data and registered intradialytic adverse events.

3. The system of claim 1, wherein the data comprises a data set having a plurality of records with measurements at a corresponding timestamp.

4. The system of claim 3, wherein the feature extraction module collects and processes the data regarding the hemodialysis session of the patient by deriving at least one of mean, standard deviation of the mean, coefficient of variance, and slope and R square of linear regression from the measurements as features of the plurality of records.

5. The system of claim 3, wherein the measurements include venous pressure and transmembranous pressure, and wherein the feature extraction module collects and processes the data regarding the hemodialysis session of the patient by deriving at least one of maximum, minimum, and mean of change rate and second-order derivative of the measurements of the venous pressure and the transmembranous pressure as features of the plurality of records.

6. The system of claim 1, wherein the machine learning model is built on a basis of a first dimension regarding targeted intradialytic adverse events for prediction and a second dimension regarding targeted time periods during the hemodialysis session for prediction.

7. The system of claim 1, wherein the machine learning model is trained by the data labeled with outcome related to the intradialytic adverse events.

8. The system of claim 1, wherein the machine learning model is trained by a key feature combination extracted from the data.

9. The system of claim 1, further comprising a data storage module configured to store the data.

10. A method for predicting an intradialytic adverse event, comprising: configuring a feature extraction module to collect and process data regarding a hemodialysis session of a patient; and configuring a model building and optimization module to build a machine learning model based on the data to predict the intradialytic adverse event during the hemodialysis session, and key features are selected and used to build the machine learning model, wherein, a first set of machine learning models are built by using a single feature from the all features, each of the first set of machine learning models is given a score based on its predicting outcome, then, top two-feature combinations are selected from a two-feature combination pool to build a second set of machine learning models, where the two-feature combination pool is established by combining the top feature selected by scores of the first set of machine learning models in the previous step with each of the remaining features, and then, the two-feature combinations selected for the second set of machine learning models that resulted in scores higher than the top score of the first set of machine learning models are kept for the next step, and then, the top three-feature combinations can be selected from a three-feature combination pool to build a third set of machine learning models, where the three-feature combination pool is established by combining the top two-feature combinations selected by scores of the second set of machine learning models with each of the remaining features, and the three-feature combinations selected for the third set of machine learning models that resulted in scores higher than the top score of the second set of machine learning models are kept for another next step, and this procedure is repeated until predetermined number of top feature combinations are selected and the predetermined number of top feature combinations are defined as the key features.

11. The method of claim 10, wherein the data regarding the hemodialysis session of the patient comprise one or more of demographic information, physiological data, dialysis data and registered intradialytic adverse events.

12. The method of claim 10, wherein the data comprise a data set having a plurality of records with measurements at a corresponding timestamp.

13. The method of claim 12, wherein the feature extraction module collects and processes the data regarding the hemodialysis session of the patient by deriving at least one of mean, standard deviation of the mean, coefficient of variance, and slope and R square of linear regression from the measurements as features of the plurality of records.

14. The method of claim 12, wherein the measurements include venous pressure and transmembranous pressure, and wherein the feature extraction module collects and processes the data regarding the hemodialysis session of the patient by deriving at least one of maximum, minimum, and mean of change rate, and second-order derivative of the measurements of the venous pressure and the transmembranous pressure as features of the plurality of records.

15. The method of claim 10, wherein the machine learning model is built on a basis of a first dimension regarding targeted intradialytic adverse events for prediction and a second dimension regarding targeted time periods during the hemodialysis session for prediction.

16. The method of claim 10, wherein the machine learning model is trained by the data labeled with outcome related to the intradialytic adverse events.

17. The method of claim 10, wherein the machine learning model is trained by a key feature combination extracted from the data.

18. The method of claim 10, further comprising configuring a data storage module to store the data.

19. A non-transitory computer readable medium, which stores a computer executable code, the computer executable code implementing the method according to claim 10 after being executed.

* * * * *